(12) United States Patent
Rodemann et al.

(10) Patent No.: US 6,645,934 B1
(45) Date of Patent: Nov. 11, 2003

(54) PEPTIDE WITH RADIO PROTECTIVE EFFECT

(75) Inventors: Hans Peter Rodemann, Stuttgart (DE); Klaus Dittmann, Tübingen (DE); Nûri Güven, Reutlingen (DE); Claus Mayer, Tübingen (DE)

(73) Assignee: Eberhard-Karls-Universität Tübingen, Tübingen (DE)

( * ) Notice: Subject to any disclaimer, the term of this patent is extended or adjusted under 35 U.S.C. 154(b) by 0 days.

(21) Appl. No.: 09/485,874

(22) PCT Filed: Jul. 1, 1998

(86) PCT No.: PCT/EP98/04051

§ 371 (c)(1),
(2), (4) Date: May 8, 2000

(87) PCT Pub. No.: WO99/09065

PCT Pub. Date: Feb. 25, 1999

(30) Foreign Application Priority Data

Aug. 16, 1997 (DE) .......................................... 197 35 587

(51) Int. Cl.⁷ .......................... C07K 14/81; C07K 7/00; A61K 38/55; A61K 7/40
(52) U.S. Cl. ................. 514/2; 514/9; 514/12; 514/15; 514/16; 424/59; 530/317; 530/324; 530/327; 530/328; 530/333; 530/344; 530/300; 435/213; 435/219

(58) Field of Search .............................. 514/2, 9, 12, 15, 514/16; 424/59; 530/317, 333, 324, 344, 327, 300, 328; 435/213, 219

(56) References Cited

FOREIGN PATENT DOCUMENTS

| WO | WO 91/07166 | 5/1991 |
| WO | WO 94/09802 | 5/1994 |
| WO | WO 94/20121 | 9/1994 |

OTHER PUBLICATIONS

Shoji Ando et al., *Anti–chymotrypsin and anti–elastase activities of a synthetic bicyclic fragment containing a chymotrypsin–reactive site of soybean Bowman–Birk inhibitor*, Biochimica et Biophysica Acta vol. 916, 1987, pp. 527–531.

Shigeyuki Terada et al., *Studies on the Synthesis of Proteinase Inhibitors*, Int. J. Peptide Protein Res., vol. 15, 1980, pp. 441–454.

Michinori Waki et al., *Synthesis and Inhibitory Properties of Reactive–Site Peptides of Protease Inhibitors from Peanut and Cucumber*, Peptide Chemistry, 1987, pp. 657–662.

*Primary Examiner*—Christopher S. F. Low
*Assistant Examiner*—Chih-Min Kam
(74) *Attorney, Agent, or Firm*—Knobbe, Martens, Olson & Bear, LLP

(57) ABSTRACT

The invention makes available a peptide having a radioprotective effect that comprises a modified form and/or an optionally modified fragment of the Bowman-Birk protease inhibitor (BBI).

2 Claims, 8 Drawing Sheets

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Peptide from the Bowman-Birk Protease
      Inhibitor.
```

```
-continued

<400> SEQUENCE: 1

Cys Ala Leu Ser Tyr Pro Ala Gln Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide from the Bowman-Birk Protease
      Inhibitor.

<400> SEQUENCE: 2

Cys Ala Leu Val Tyr Pro Ala Gln Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Peptide from the Bowman-Birk Protease
      Inhibitor.

<400> SEQUENCE: 3

Ala Leu Ser Tyr Pro Ala Gln
1               5
```

PEPTIDE WITH RADIO PROTECTIVE EFFECT

This application is the U.S. National Phase under 35 U.S.C. §371 of International Application No. PCT/EP98/04051, filed Jul. 1, 1998, The present invention relates to a peptide having a radioprotective effect.

A peptide of this kind is known, for example, from the publication of K. Dittmann et al. (1995): "Bowman-Birk Protease Inhibitor (BBI) modulates radiosensitivity and radiation-induced differentiation of human fibroblasts in culture," Radiotherapy and Oncology 34, pages 137–143.

A "radioprotective effect" of a peptide is understood to mean its protective activity for cells, tissue, or organisms with respect to harmful or injury-causing radiation. For living organisms in particular, harmful radiation is ionizing radiation as well as UV radiation, i.e. energy-rich types of radiation. A peptide exhibits a radioprotective effect if the injury brought about by radiation is reduced by that peptide. The underlying mechanisms of a radioprotective effect are at present still entirely unexplained.

The injury brought about by energy-rich radiation includes, for example, alteration of DNA (i.e. mutagenesis) that can result in tumor formation, but also the degeneration, atrophy, fibrosis, or necrosis of tissues exposed to high levels of radiation.

For example, the occurrence of malignant melanoma is promoted by high levels of sunlight on the skin.

The human body is confronted with particularly high radiation intensities not only when exposed to a great deal of sunlight, but also during X-ray diagnosis or in the context of radiation therapy of tumor diseases.

Protection against UV radiation is offered, for example, by UV-filtering substances such as those contained, for example, in suntan lotion. In order to protect against ionizing radiation, body parts that are not to be irradiated are shielded, and the radiation is applied in as precisely localized a fashion as possible.

It has recently been recognized that there are peptides which can exert a radioprotective effect. One such peptide is the aforementioned Bowman-Birk Protease Inhibitor (BBI), an inhibitor of the serine proteases trypsin and chymotrypsin that has been known for some time and that is present in large quantities in soybeans.

The amino acid sequence of BBI is known, and by 1984 the corresponding soybean gene had already been cloned (R. W. Hammond (1984): "Molecular Cloning and Analysis of a Gene Coding for the Bowman-Birk Protease Inhibitor in Soybean," J.Biol.Chem. 269, pages 9883–9890).

BBI comprises 71 amino acids and has a molecular weight of approximately 8,000 daltons. One of the characteristics of BBI is the presence of fourteen cysteine residues, which form seven disulfide bonds and thus make a substantial contribution to determining the folding or secondary structure of BBI.

By chemical and enzymatic cleavage with cyanogen bromide (CNBr) and the protease pepsin, BBI is split into two halves, one of which exhibits the trypsin-inhibiting activity, and the other the chymotrypsin-inhibiting activity (S. Odani and T. Ikenaka (1978): "Studies on Soybean Trypsin Inhibitors," J. Biochem. 83, pages 747–753).

In addition to the protease inhibitor function, two additional physiological activities of BBI have been demonstrated, namely an anticarcinogenic effect and the radioprotective effect already mentioned.

In the publication of B. H. St.Clair, (1990): "Suppression of Dimethylhydrazine-induced Carcinogenesis in Mice by Dietary Addition of the Bowman-Birk Protease Inhibitor," Cancer Research 50, pages 580–586, it was shown that BBI has an anticarcinogenic effect. In vitro studies with cultivated cells demonstrated that the chymotrypsin-inhibiting domain could prevent malignant transformation of the cells. In vivo studies, on the other hand, in which tumors were induced in mice using carcinogens and in which BBI was administered orally, showed that the trypsin-inhibiting domain of BBI is necessary in order to suppress tumor formation. This anticarcinogenic effect is therefore attributed directly to the protease-inhibiting effect of BBI. It was further demonstrated in the in vivo studies that BBI which had been autoclaved, i.e. thermally denatured, no longer possessed an anticarcinogenic effect.

The aforementioned radioprotective effect of BBI was described in the publication of Dittmann et al. cited above. It was demonstrated in this instance that BBI decreases the radiation-induced mortality of cultivated human fibroblasts (connective tissue cells that occur in large numbers, for example, in the skin).

U.S. Pat. No. 5,376,373 has proposed a method in which the weight loss and hair loss caused by radiation is inhibited by oral administration of a "concentrate," obtained from soybeans, that contains BBI. Isolation of the BBI concentrate involves repeated fragmentation, precipitation, ultrafiltration, dilution, and reconcentration of a soybean extract in order to obtain the radioprotective product. It is not known which additional constituents, for example additional protease inhibitors or the like, are contained in the concentrate.

One problem involving oral intake of BBI with food is the fact that it has been demonstrated in rats that large quantities of trypsin inhibitors result in hypertrophy and hyperplasia of pancreatic cells, and in loss of body weight. Rats that ingested trypsin inhibitors from soybeans for long periods in fact developed pancreatic tumors.

A further problem with the administration of serine protease inhibitors, especially with intravenous administration, is the fact that blood clotting, in which serine proteases play a substantial role, can be disturbed.

In view of the above, it is an object of the present invention to make available a peptide having a radioprotective effect and which can be produced with little effort and in which the disadvantages of the previously known radioprotective products are avoided.

This object is achieved, according to the present invention, in that a peptide having a radioprotective effect comprises a modified form and/or an optionally modified fragment of the Bowman-Birk Protease Inhibitor.

Specifically, the inventors have found, surprisingly, that structurally modified forms and even fragments of BBI also possess a radioprotective activity. It is now therefore no longer necessary to make BBI available in its native form in order to obtain a peptide having the desired radioprotective effect.

In this context, modified is understood for the purposes of the invention to mean any change in the structure or conformation of BBI and any alteration in its amino acid sequence, whether by chemical or enzymatic insertion or removal of individual groups of amino acids or by the exchange of individual amino acids. A modified form of BBI also encompasses a peptide in which further amino acids are appended onto the N-terminal or C-terminal end of the BBI, for example domains of further proteins or peptides which facilitate purification of the BBI and/or enhance its radioprotective effect even further.

A fragment for the purposes of the invention is understood to mean any portion of the BBI in which either only individual amino acids or larger amino acid segments of the BBI are missing. Such fragments comprise, for example, individual domains of the BBI. According to the present invention, such fragments can also be modified in the sense discussed above.

Modified forms of BBI or BBI fragments can be produced either by treatment of the native (i.e. unaltered) BBI with chemicals or enzymes, or by synthesis with chemical or molecular biological methods.

The fact that modified forms or fragments of BBI can also have a radioprotective effect was not to be expected, since modifications, especially if they involve the conformation of the peptide, usually destroy or at least greatly reduce the physiological activity of a peptide.

In addition, with respect to the anticarcinogenic activity of BBI it had been shown that impairment of the BBI structure by thermal denaturing caused its anticarcinogenic effect to be completely lost.

Modified forms or fragments of BBI can be handled without difficulty, since there is no need to ensure, during either manufacture or storage, that any contact with modifying agents, proteases, or the like is excluded.

The object underlying the invention is thus completely achieved.

In a preferred embodiment, the new peptide has no protease-inhibiting effect against trypsin and chymotrypsin.

A peptide of this kind has the considerable advantage, in addition to the radioprotective effect, of not at the same time additionally blocking the proteases trypsin or chymotrypsin. This is advantageous in particular if the peptide is to be used to protect cells, tissue, or organisms against radiation, since—as already explained above—at least peptides having a trypsin-inhibiting effect are harmful to pancreatic cells and can even result in tumor formation.

The fact that modified forms of BBI are radioprotectively effective without at the same time having a protease-inhibiting activity against trypsin and chymotrypsin was all the more astonishing in that it had hitherto been assumed that one of these protease-inhibiting domains was necessary for the further activity of BBI, namely its anticarcinogenic effect (St.Clair et al., 1990).

A peptide according to the present invention has a single well-defined effect, namely protection against radiation. If it is used in the presence of trypsin and chymotrypsin, the activity of these serine proteases is not simultaneously impeded. The aforesaid pancreas-damaging side effects are thus also prevented.

In a further preferred embodiment, the peptide has at least two cysteine residues that are present in reduced form.

The advantage of this feature is that a peptide of this kind can be used as a radioprotective agent even in the presence of reducing agents. In peptides which contain cysteine residues, reducing agents cause their sulfur radicals to become protonated and thus to be present as SH groups. Under oxidizing conditions, the SH groups form disulfide bonds which play an essential role in determining the folding of the peptide.

Reducing agents are often used in the purification of proteins and peptides. Under physiological conditions, reducing conditions exist in the interior of cells due to the presence of glutathione.

The availability of a peptide whose cysteine groups or residues are present in reduced form has the further advantage that it can be produced without difficulty using molecular biological methods in bacteria. Expression of this kind in bacteria is substantially easier and more efficient as compared to expression in yeasts and higher eukaryotic cells, and allows particularly high yields. This system is unsuitable, however, for proteins or peptides in which the cysteine residues are covalently bound to one another via disulfide bonds, since disulfide bonds cannot be formed in bacteria. A reduced form of BBI, on the other hand, can readily be expressed in bacteria.

In a further preferred embodiment, at least some of the amino acid groups of the peptide are present in alkylated form.

"Alkylation" is understood to mean the modification of individual amino acids with alkyl groups, usually methyl groups. This modification is performed with so-called alkylation reactions, for example with iodoacetamide.

Treating the BBI with iodoacetamide after reduction of the disulfide bonds adds a methyl group to the SH groups of the cysteine, i.e. alkylates them. Reoxidation of the SH groups is then no longer possible. This therefore prevents the disulfide bonds from being formed again even under oxidizing conditions.

Alkylation of BBI or of BBI fragments has the advantage that the cysteine residues are obtained in their reduced form, and are thus stabilized.

In a further preferred embodiment, the peptide has less than 20, and very preferably less than ten amino acids.

A BBI fragment of such drastically diminished size has the considerable advantage that when it is used on cells, tissue, or in the entire organism, because of its small size it becomes distributed and penetrates much better and more quickly than complete BBI, which comprises more than 70 amino acids.

Good distribution and easy penetration into the tissue is essential when the peptide is used as a radioprotector, since it can then quickly and comprehensively exert its protective effect against radiation.

In a further preferred embodiment, the peptide is a nonapeptide and has the sequence SEQ ID NO: 1 from the appended Sequence Listing.

As is evident from the Preferred Embodiments, the inventors have succeeded in demonstrating that this nonapeptide exerts just as great a radioprotective effect on human fibroblasts as does complete BBI. The use of a peptide much smaller in size compared to complete BBI, comprising only nine amino acids (nonapeptide), has the substantial advantage that this nonapeptide can be produced more easily. The reason is that a nonapeptide can be produced without difficulty by chemical synthesis, also called Merrifield synthesis. This type of peptide synthesis is a common and well-established synthesis method with which a peptide of this kind can be obtained in large quantities and at high purity.

In a further preferred embodiment, the peptide is a nonapeptide having the sequence SEQ ID NO: 2 from the appended Sequence Listing.

With this nonapeptide, the sequence taken from the naturally occuring BBI has been altered by one amino acid. The serine from the sequence SEQ ID NO: 1, i.e. a hydrophilic amino acid, has been replaced in SEQ ID NO: 2 by a valine, i.e. a hydrophobic amino acid. A radioprotective effect has been demonstrated for this modified peptide as well, as is evident from the Preferred Embodiments. This modified nonapeptide having the sequence SEQ ID NO: 2 can also be synthesized without difficulty via Merrifield synthesis.

In a further preferred embodiment, the terminal cysteine groups of the peptides having sequences SEQ ID NO: 1 and 2 are covalently bound together.

This yields ring-shaped or cyclic peptides that exhibit excellent stability in an oxidizing medium. An oxidizing medium exists, for example, in the extracellular matrix of connective tissue and in all parts of the body that are in contact with outside air.

Since both the linear and the cyclic peptides having the sequences SEQ ID NO: 1 and 2 exhibit a radioactive protective effect, they are effective as radiation protection in both a reducing and an oxidizing environment and are thus universally usable.

In a further preferred embodiment, the peptide has the sequence SEQ ID NO: 3 from the appended Sequence Listing.

This peptide comprises only seven amino acids, i.e. is a heptapeptide. Because the peptide is further shortened while retaining its radioprotective effect, the peptide can be produced even more quickly and economically, and can be applied more easily.

All peptides having the sequences SEQ ID NO: 1 through 3, whether they are ring-shaped or linear, have the considerable advantage of having no protease-inhibiting activity. They can thus be used without the undesirable side effect of blocking the digestive enzyme trypsin and chymotrypsin, and other serine proteases.

In a further preferred embodiment, at least one of the amino acids of the peptide has a protective group.

Protective groups of this kind can be any protective groups known in peptide chemistry; it is preferred that the C-terminal amino acid has an acetyl group and/or that the N-terminal amino acid has an amide group.

These protective groups have the advantage of protecting the peptide from the attack of exopeptidases, so that the peptides have substantially greater stability in a biological medium such as, for example, in cell culture or in the organism. Protective groups that block the C-terminal carboxyl group and the N-terminal amino group of peptides, such as the aforesaid acetyl and amide groups, furthermore ensure that the peptides do not form any further peptide bonds with other peptides or with one another, so that tandemizing of the peptides is also reliably prevented. When several peptides are linked to one another, it can no longer be assumed with certainty that the radioprotective effect still exists.

The protective groups thus also ensure that the peptides retain their radioprotectively effective structure.

A further aspect of the present invention is the use of one or more of the aforesaid peptides as a radioprotective agent.

This use as a radioprotective agent comprises any use in which the peptides are utilized for protection against radiation, whether ionizing radiation, UV radiation, or electromagnetic radiation.

In a particularly preferred fashion, a peptide according to the present invention is used for protection against ionizing radiation, in particular of normal tissue in radiation therapy of tumor patients.

Specifically, in radiation therapy of this kind, ionizing radiation is used to treat usually malignant tumors. The intention in this context is to inflict maximal damage on the tumor tissue and at the same time to minimize damage to the surrounding healthy normal tissue.

In order to minimize stress on the normal tissue, the radiation is used locally when possible. Protection of the normal tissue located in the immediate vicinity of the tumor tissue is, however, very problematic. A peptide according to the present invention is ideal for use here, since it can be used either locally or, for example via the blood circulation, in generalized fashion. In particular with the small peptides having the sequences SEQ ID NO: 1 through 3, rapid and homogeneous distribution into the tissues is achieved, and thus also rapid protective effect with respect to the radiation. In addition, all the peptides according to the present invention exhibit excellent stability and at the same time radioprotective effectiveness in both oxidizing and reducing environments, which additionally enhances their therapeutic usefulness.

A peptide according to the present invention is preferably also used against UV radiation, in particular against the UV radiation of sunlight.

It is advantageous in this context that the peptides are highly stable even under oxidizing conditions, i.e. for example in air, and can exert a long-lasting protective effect against UV radiation. They are thus suitable for use as a skin protection against high levels of solar irradiation. The use of the nonapeptides and heptapeptide according to the present invention has the further advantage that because of their small size, the peptides can penetrate into the skin and are stable therein for a long period.

The invention moreover concerns a pharmaceutical composition, in particular for intravenous administration, that contains one or more of the peptides according to the present invention in a radioprotectively effective quantity.

For this purpose, the peptides can be prepared in the galenicals that are appropriate and usual in each case. In addition to intravenous administration, consideration can also be given to percutaneous administration or local injection into, for example, body areas or body cavities directly affected by irradiation.

With a pharmaceutical composition of this kind, it is advantageous that the peptides exert their radioprotective effect without at the same time triggering dangerous immune reactions. The reason is that because of their small size, the peptides according to the present invention have very little immunogenicity, so that in normal circumstances no allergic reactions may be expected when the pharmaceutical composition is used on the human or animal body, and the peptides are also not eliminated from the organism in question by the action of antibodies.

The invention also concerns a cosmetic composition for application onto the skin which is characterized in that it contains one or more of the peptides according to the present invention in a radioprotectively effective quantity.

A cosmetic composition of this kind can be provided, for example, as a suntan lotion, skin creme, or the like, and then contains the usual constituents of such compositions, such as oils, emulsions, pigments, etc. It is understood that the cosmetic composition can additionally contain UV filters such as derivatives of p-aminobenzoic acid, salicylic acid, cinnamic acid, dibenzoylmethane, or the like.

Because of the radioprotective effectiveness of the peptides according to the present invention, a cosmetic composition of this kind offers ideal protection against, in particular, the UV radiation of sunlight. Since the peptides according to the present invention, because of their small size, in fact penetrate into the skin and moreover are stable for a long period, long-term protection against radiation can thus be achieved.

The invention further concerns a nucleic acid that has a sequence segment coding for a peptide according to the present invention, and optionally has control sequences necessary for expression of the nucleic acid.

A nucleic acid of this kind is advantageously used to produce a peptide according to the present invention using molecular biological techniques, for which purpose it is preferably contained in an expression vector.

The production of a peptide according to the present invention by nucleic acid expression has the advantage of being a particularly simple possibility for manufacturing the peptide in practically unlimited quantities and for easily converting it by modifying the corresponding coded sequence at the nucleic acid level. A number of standard methods for this are known, for example in vitro mutagenesis, site-directed mutagenesis, oligonucleotide synthesis, PCR, etc.

The expression system used can be either an in vitro expression system, for example a reticulocyte lysate, or in vivo expression in bacteria, yeasts, or eukaryotic cells, suitable expression vectors being used in each case. Since the formation of disulfide bonds is not absolutely necessary for the radioprotective effect of the peptides according to the present invention, expression can occur in bacteria, in which disulfide bonds are not formed.

To facilitate the manufacture and purification of the peptides according to the present invention, they can also be synthesized as fusion peptides; this means that sequences coding for amino acid segments or domains of known proteins are fused onto the nucleic acids according to the present invention, the result being that one continuous peptide is then produced upon expression. Examples of such fused-on amino acid segments are, for example, so-called histidine tags, with which expressed fusion proteins can be purified using nickel chelate columns, or antigenic determinants, with which the peptides can be purified using suitable antibody affinity columns.

In an alternative preferred method for producing a peptide according to the present invention, the native BBI is cleaved proteolytically and/or chemically.

The starting point for this method can be a BBI purified from soybeans or BBI manufactured by molecular biology; and the radioprotectively effective modified forms or fragments of the BBI are obtained therefrom by (bio)chemical methods. It is possible in this context to use, for example, proteases that cleave the BBI, for example pepsin, and/or chemical cleavage can be accomplished using cyanogen bromide.

It is understood that the features mentioned above and those yet to be explained below can be used not only in the respective combinations indicated, but also in other combinations or alone, without leaving the context of the present invention.

Further advantages are evident from the Embodiments which follow and in conjunction with the drawings, in which.

EXAMPLE 1

Radioprotective Effect and Protease-inhibiting Activity of BBI and of Modified BBI Forms A Radioprotective Effect The examination of the radioprotective effect of BBI and of modified forms of BBI was performed as a so-called clonogenic assay, which is described, for example, in K. Dittmann et al., Radiotherapy and Oncology 34 (1995), pages 137–143, and is explained briefly below.

1.1 Clonogenic Assay

Normal human fibroblasts were cultivated in Dulbecco's Modified Eagles Medium (DMEM) with 10% fetal calf serum under standard conditions. At each cell passage the number of cells was counted, and the cells were seed with a density of $2 \times 10^4/cm^2$ when subcultures were set up.

For the clonogenic assay, secondary fibroblasts were trypsinated with 0.05% trypsin and 0.1 EDTA, and seed at a cell density of 50 cells per $cm^2$ into six-well tissue culture dishes. The cells were cultivated with 2 ml DMEM with 20% fetal calf serum per well.

After 24 hours the medium was removed and the cells were incubated for 16 hours either in additive-free control mediums ("0" in the Figures) or in medium that contained 10 $\mu$M of either BBI or a modified BBI form or a BBI fragment. The nonapeptides and heptapeptide according to the present invention (see Example 3) were used at a concentration of 80 $\mu$M.

This was followed by irradiation with ionizing radiation, the energy dose being either 2 or 4 gray (Gy). This energy dose corresponds to the entire converted radiation energy given in mass unit Joule/kg=(gray). A 6 MeV linear accelerator (Mevatron, Siemens) was used for irradiation.

The cells were then cultivated for a further eight days in BBI-free culture medium in order to allow colonies to form. The cells were then fixed, stained, and counted; in the Figures, "K" indicates the absolute number of clones counted.

A clone is a colony or a cell cluster resulting from the division of one cell during the eight-day cultivation period. The number of clones corresponds to the degree to which the human fibroblasts survived the irradiation. This will therefore also be referred to hereinafter as the "clonogenic survival" of the cells. If many cells die when the cells are irradiated, then only a few clones will form after eight days; if many cells survive, then many clones may be counted after eight days of cultivation. The clonogenic survival of the cells after irradiation is thus a direct indication of the radioprotective effect of the BBI product being used.

1.2 Radioprotective Effect of BBI and of Modified BBI Forms

Figure 1:
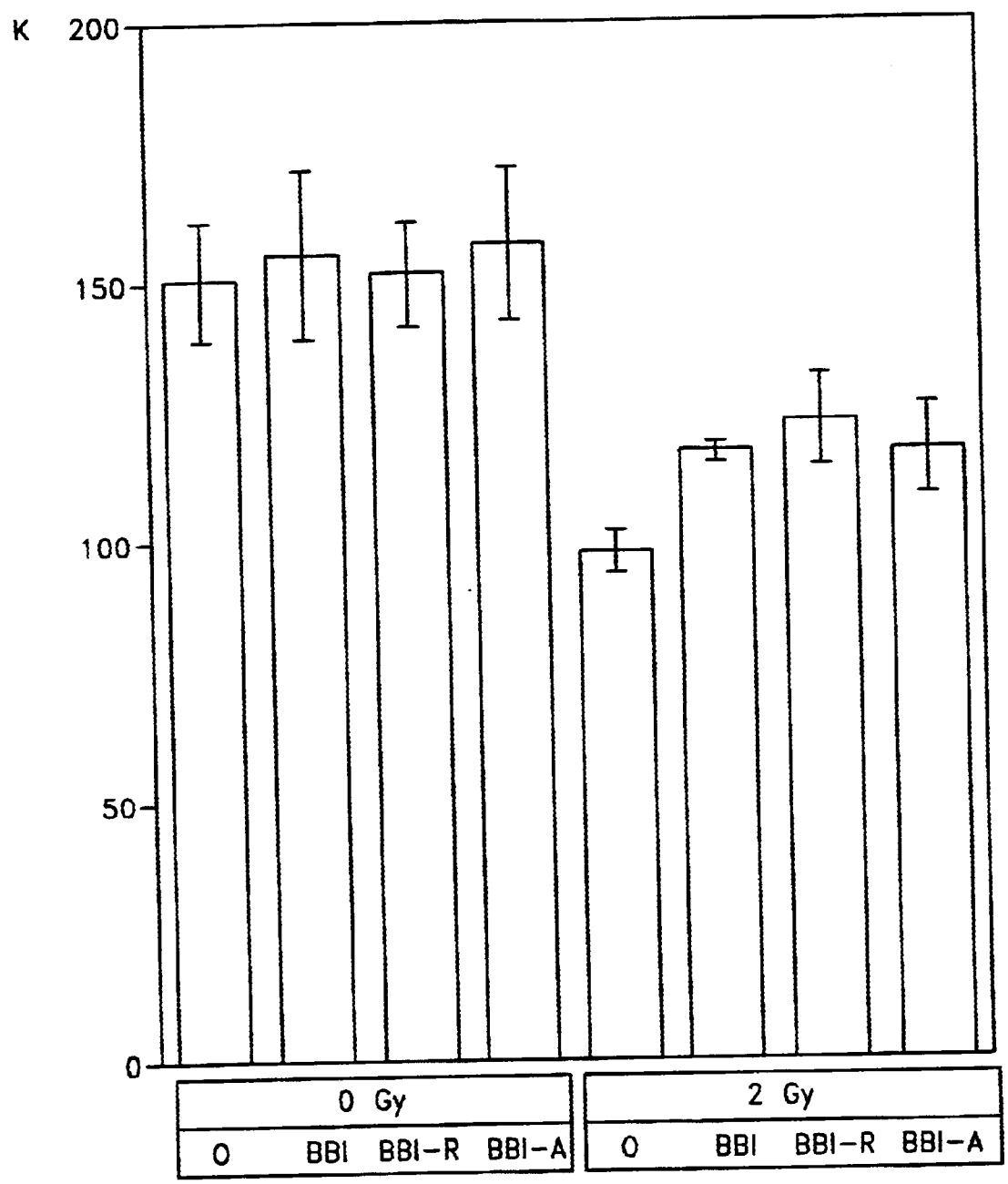
FIG. 1 shows the result of a so-called clonogenic assay with native and modified BBI, in the form of a bar chart.

Four different batches were tested in the clonogenic assay whose results are shown in FIG. 1. In the control batch labeled "0" no BBI was used. In the batch labeled "BBI", complete BBI (from Sigma Biochemicals) was used; and in the batch labeled "BBI-R" the complete BBI was pretreated with the reducing agent dithiothreitol (DTT), so that all the disulfide bonds in the BBI were cleaved.

In the batch labeled "BBI-A", the BBI was first reduced and the cysteine residues were then alkylated with iodoacetamide in order to prevent reoxidation of the cysteine residues. To perform this reduction, 8 mg BBI in 0.5 ml PBS and 0.2 ml denaturing buffer (12.5 mM TRIS pH 6.8, 80 $\mu$l EDTA, 1% SDS, and 20% glycerol) was boiled for 10 min in 20 $\mu$l fresh 2.6 M DTT solution. After reduction, alkylation was performed for 60 minutes at 20° C. by adding 70 $\mu$l 20% iodoacetamide solution. The batches were then dialyzed four times against PBS for 24 hours.

The four batches (0, BBI, BBI-R, and BBI-A) were either not treated with ionizing radiation (0 Gy) or were irradiated with a single dose of 2 Gy.

This test was repeated in several independent experiments, and the results were each averaged. The error bars indicate the variation in the values.

As is evident from FIG. 1, without irradiation (0 Gy) the addition of BBI, reduced BBI, or reduced and alkylated BBI does not influence survival of the cells within experimental error. Without the addition of BBI (0), the clonogenic survival of human skin fibroblasts after irradiation with a single dose of 2 Gy is reduced by approximately 30 to 40%.

A 16-hour pretreatment with BBI (BBI), reduced BBI (BBI-R), or reduced and alkylated BBI (BBI-A) resulted in a significant increase (20–30%) in the clonogenic survival of the irradiated human skin fibroblasts.

Significant differences between BBI, BBI-R, and BBI-A were not detectable within experimental error.

The results of the clonogenic assay shown in FIG. 1 confirm that modified forms of BBI, namely its reduced form or reduced and alkylated form, have just as great a radioprotective effect as unmodified BBI.

B Inhibitor Effect

The next aspect studied was whether or not the modified forms of BBI acted as protease inhibitors with respect to chymotrypsin. This was done by performing a protease inhibition test which is explained briefly below.

1.3 Protease Inhibition Test

A batch containing 50 µl TLCK-treated chymotrypsin (0.1 mg/ml) was incubated for 10 minutes in 12.5% DMSO and 87.5% PBS with 50 µl of a solution having BBI (BBI), reduced BBI (BBI-R), or reduced and alkylated BBI (BBI-A) together with 50 µl PBS and 50 µl of the chymotrypsin substrate acetyl-A-A-P-F-pNa (0.5 mg/ml, of Bachem Heidelberg, Germany). The colored reaction product was detected at 405 nm in a spectrophotometer.

If inhibition of the protease trypsin (see Example 4, FIG. 8) was to be determined, TPCK-treated trypsin (0.1 mg/ml) and the peptide CBZ-R-pNa (1 mg/ml) as substrate were used, and the test was otherwise performed as described.

A batch without BBI (0) was run as control, and its measured value was taken as 100% chymotrypsin activity (% CH). The blank value with buffer alone is labeled "-" and indicates the cuvette and buffer solution background.

1.4 Inhibition of chymotrypsin by BBI and modified BBI

Figure 2:
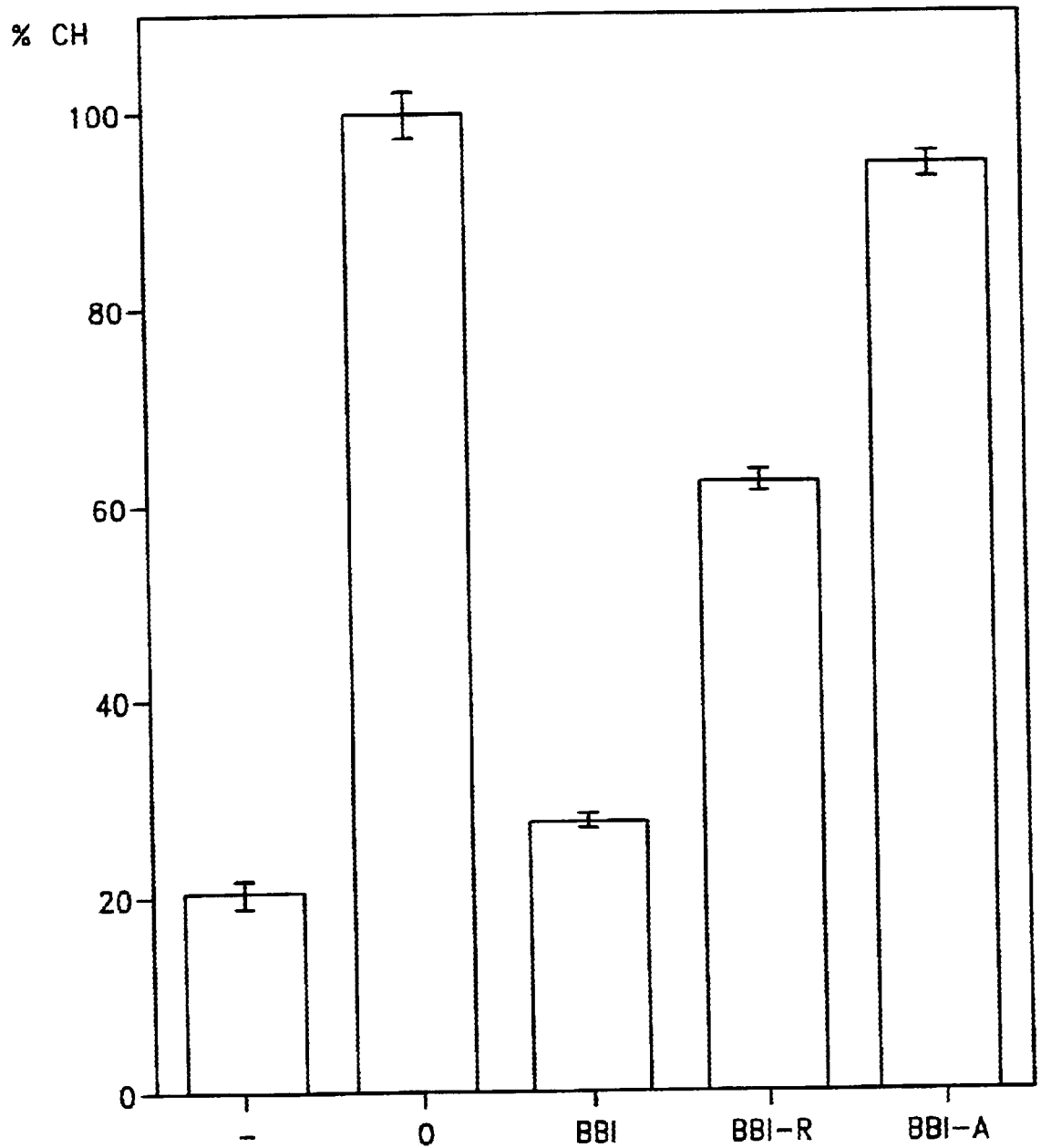
FIG. 2 shows, as a bar chart, the chymotrypsin-inhibiting activity of native and modified BBI.

The results of the chymotrypsin test are shown in FIG. 2. Whereas complete BBI produces 80% inhibition of chymotrypsin activity, the reduced form of BBI (BBI-R) can inhibit chymotrypsin activity by only about 30%. The reduced and alkylated form of BBI (BBI-A), on the other hand, is no longer capable of inhibiting chymotrypsin activity.

The undesirable side effect occurring when the modified forms of BBI (BBI-R and BBI-A) are used as radioprotective agents—namely that chymotrypsin, a digestive enzyme, is simultaneously inhibited—is thus greatly reduced or completely absent with the modified BBI forms.

EXAMPLE 2

Cleavage of BBI with Cyanogen Bromide and Pepsin, and Analysis of the Cleavage Products for Protease Inhibition and Radioprotective Activity This experiment demonstrated that fragments of BBI also have a radioprotective effect.

2.1 Cleavage of BBI

Complete BBI was digested with cyanogen bromide (CNBr) and with the stomach enzyme pepsin. This was done by diluting 50 mg BBI in 1.5 ml formic acid of 70%. Then 118 mg cyanogen bromide were added and the assay was incubated at 4° C. for 20 hours. The reaction mixture was diluted with water and lyophilized. The lyophilisate was then digested with 340 U pepsin at pH 2.5 for 24 hours at 40° C. Formic acid was added to stop the digestion reaction.

2.2 Separating the Cleavage Products

The cleaved material was then separated by molecular sieve chromatography on a Sephadex G25 column. The column run yielded 110 fractions, whose inhibitory activity with respect to trypsin or chymotrypsin was studied in the protease inhibition test discussed in section 1.3.

2.3 Protease Inhibition

Figure 3:
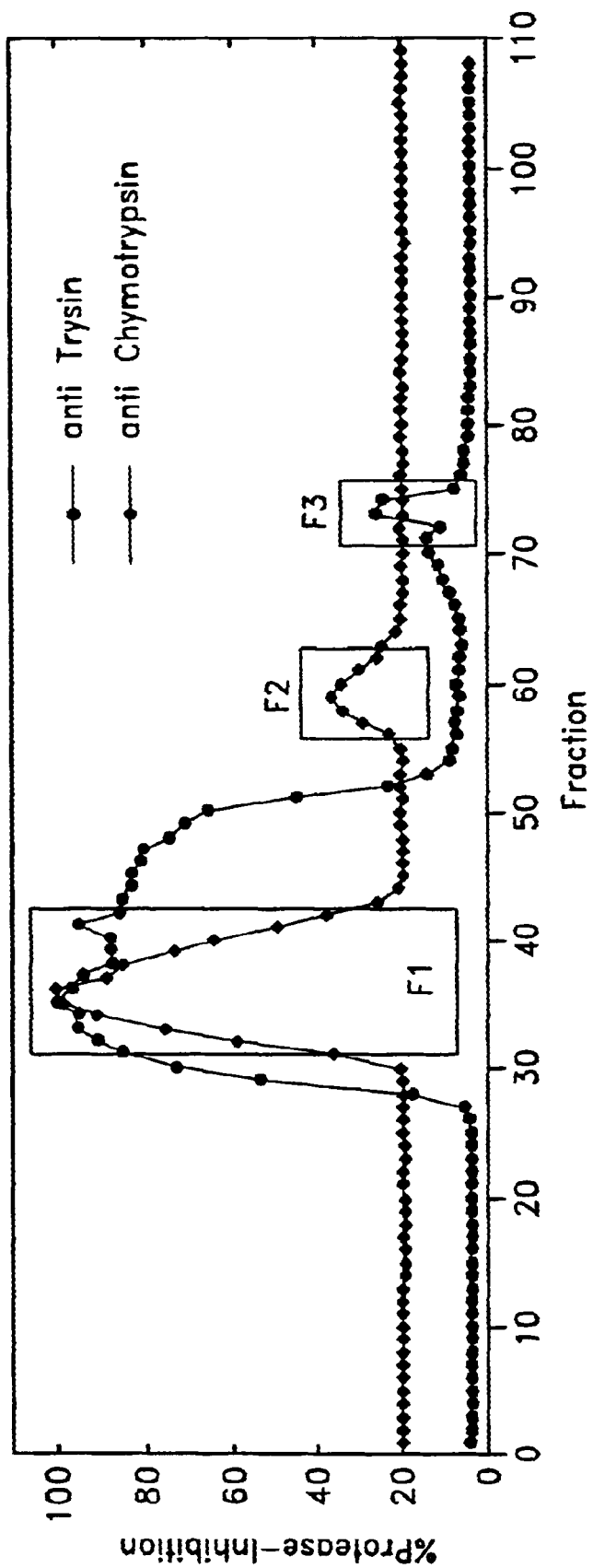
FIG. 3 shows the elution profile of a chromatographic separation of BBI and BBI fragments.

FIG. 3 shows the results of protease inhibition of the individual column fractions; the circle symbols indicate trypsin-inhibiting activity (anti-trypsin), and the diamond symbols indicate chymotrypsin-inhibiting activity (anti-chymotrypsin).

A total of three peaks appeared: one peak (F1) at fractions 30–50, in which both trypsin-inhibiting activity and chymotrypsin-inhibiting activity were detectable; a further peak (F2) at fraction 60, in which chymotrypsin-inhibiting activity was detectable; and a third peak (F3) at fraction 72–73, in which chymotrypsin-inhibiting activity was detectable.

The fractions contained in the first peak (F1) contain predominantly uncleaved complete BBI, which inhibits both trypsin and chymotrypsin. The fractions labeled F2 and F3 contain two cleavage products of BBI, the cleavage product with chymotrypsin-inhibiting activity (F2), and the cleavage product with trypsin-inhibiting activity (F3).

2.4 Clonogenic Assay

The three fractions F1, F2, and F3 were used in a clonogenic assay as has been described in section 1.1. Prior to irradiation with a single dose of 2 Gy, the skin fibroblasts were treated with fractions F1 through F3 for 16 hours; their clonogenic survival was then analyzed by comparison to irradiated control cells (0) with no added BBI product.

Figure 4:
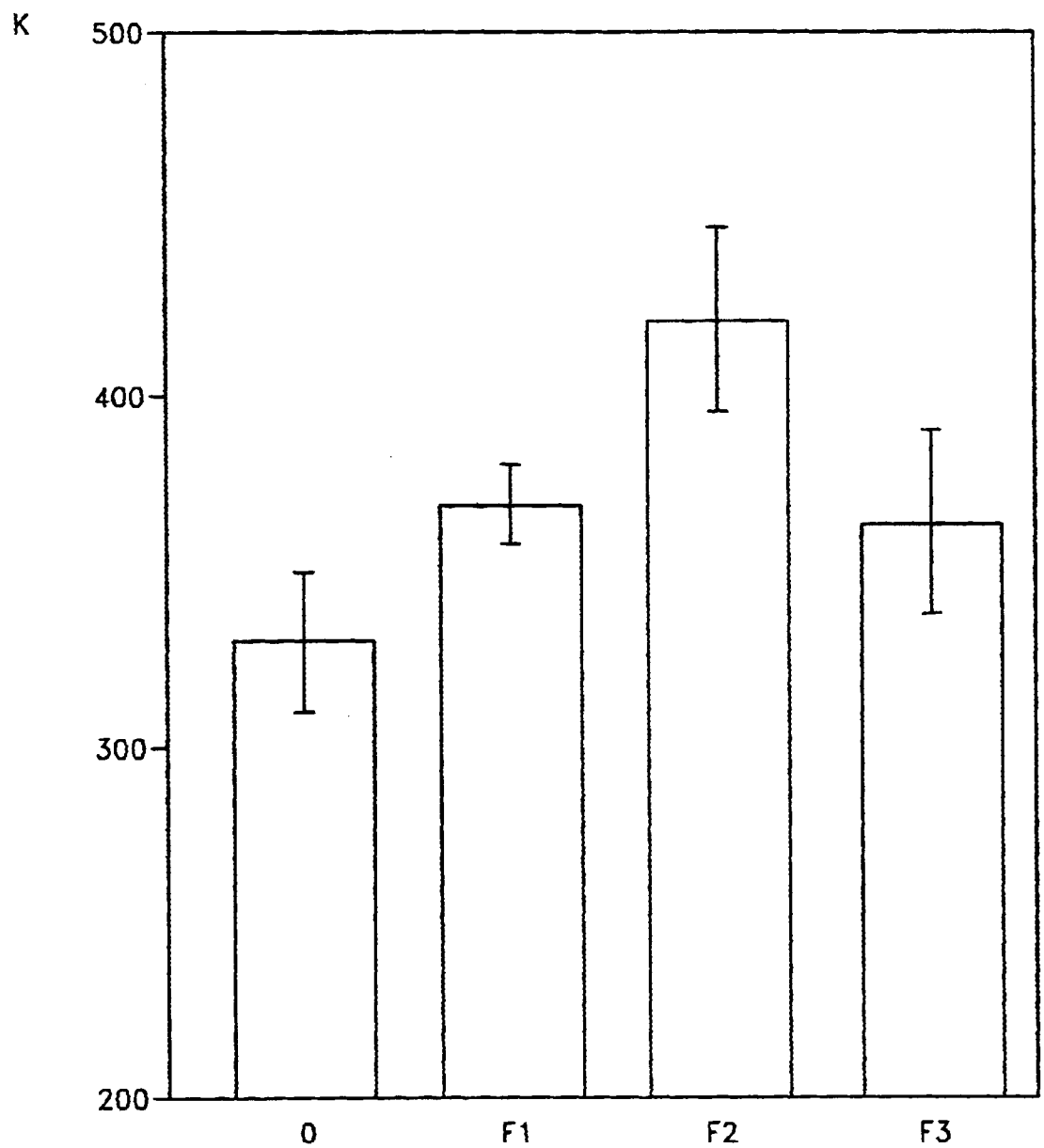
FIG. 4 shows, as a bar chart, the result of a clonogenic assay with selected fragments of the chromatograph of FIG. 3.

As shown in FIG. 4, all three fractions exhibited a definite increase in clonogenic survival, wherein fraction F2, i.e. the cleavage product having the chymotrypsin-inhibiting activity, in fact exhibited a substantially greater radioprotective effect than uncleaved complete BBI (F1) or the cleavage product having trypsin-inhibiting activity (F3).

The results reported here demonstrate that peptide fragments of BBI produced by chemical and enzymatic cleavage exert a radioprotective effect as great as or even substantially greater than that of complete BBI.

EXAMPLE 3

Radioprotective Effect of the Nonapeptides and Heptapeptide According to the Present Invention In a further clonogenic assay (see section 1.1), the radioprotective effect of a total of four BBI fragments according to the present invention was tested against complete BBI.

The substances used in the test were complete BBI (BBI) and four peptides, chemically synthesized by Merrifield synthesis, whose C-terminal amino acids had acetyl groups as protective groups, while their N-terminal amino acids had amide groups as protective groups. The sequences of these peptides are described in the appended Sequence Listing.

Peptide P1 has the sequence SEQ ID NO: 1, wherein its terminal cysteine residues are crosslinked with a disulfide bond, so that peptide P1 has a ring structure. Peptide P2 has the sequence SEQ ID NO: 3; it contains no cysteine residues and therefore assumes a linear conformation.

Peptide P3 corresponds to peptide P1, i.e. has the sequence SEQ ID NO: 1, but its terminal cysteine residues are not cross linked with a disulfide bond.

Peptide P4 has the sequence SEQ ID NO: 2, and thus exhibits a serine→valine amino acid exchange as compared to peptides P1 and P2 that have the sequence SEQ ID NO: 1. Its terminal cysteine residues are not crosslinked with a disulfide bond, so that peptide P4 also has a linear structure.

Peptides P1, P3, and P4 are nonapeptides having nine amino acids, whereas peptide P2 is a heptapeptide having only seven amino acids.

Figure 5:
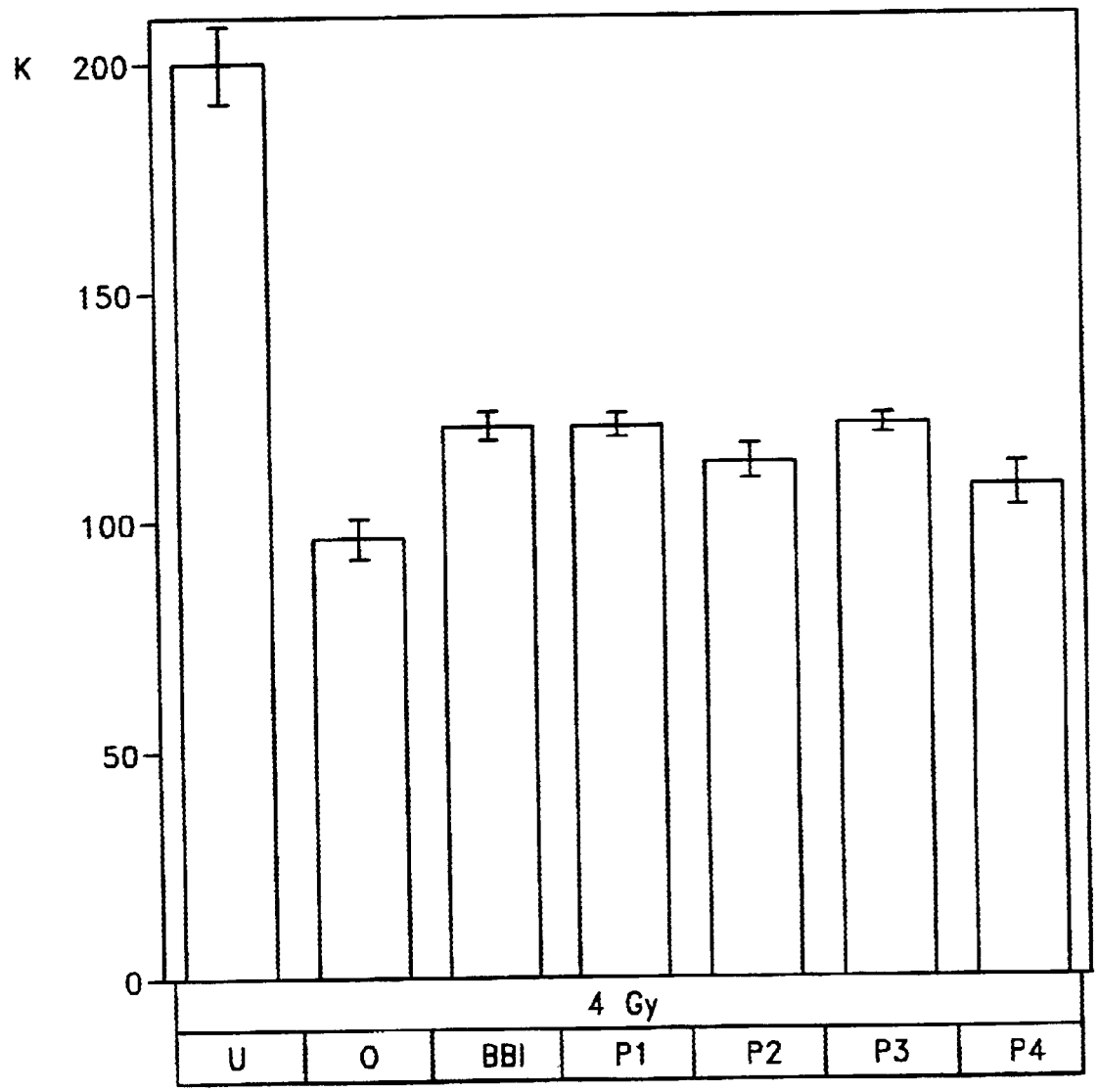
FIG. 5 shows, as a bar chart, the results of a clonogenic assay with BBI and with four peptides according to the present invention, under ionizing radiation.

FIG. 5 shows the results of the clonogenic assay. One change as compared to the procedure described in section 1.1 is the fact that irradiation of the fibroblasts was performed with a single dose of 4 Gy.

In addition to the batches in which complete BBI and the peptides P1–P4 were used, two control batches were also run: one was a batch with unirradiated fibroblasts with no added BBI or peptide (U), and the other a batch with irradiated fibroblasts but also with no addition of BBI or of any of the peptides (0).

The complete BBI was used at a concentration of 10 $\mu$M, and peptides P1–P4 each at a concentration of 80 $\mu$M.

As is evident from FIG. 5, all the peptides exhibited a radioprotective effect comparable to that of complete BBI. Peptides P1 and P3, i.e. the linear and circular forms of the sequence SEQ ID NO. 1, had an even more pronounced radioprotective effect than peptides P2 (heptapeptide) and P4 (with exchanged bases).

The peptides according to the present invention thus exhibit, for human skin fibroblasts, a protective effect against ionizing radiation which is comparable to that of complete BBI (which is eight to ten times larger in size).

Figure 6:
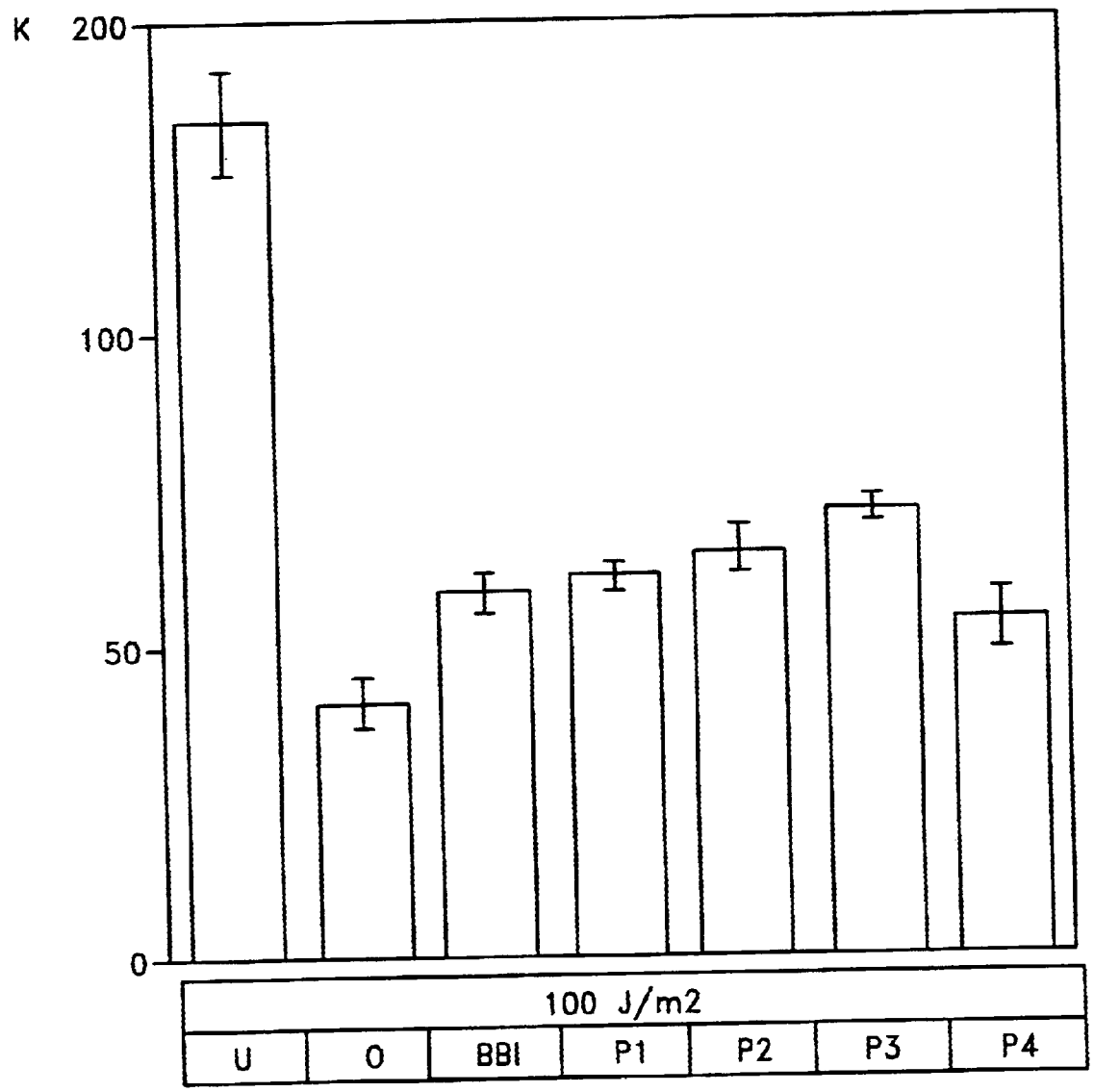
FIG. 6 shows, as a bar chart, the result of a clonogenic assay with BBI and with four peptides according to the present invention, under UV irradiation.

FIG. 6 shows that the peptides exert, not only against ionizing radiation but also against UV radiation, a protective effect that is also as great as or greater than that of complete BBI.

Once again a clonogenic assay was performed, using complete BBI or the four peptides P1 through P4.

In this case irradiation was performed with UV-B radiation at 100 J/m$^2$.

When complete BBI was used, clonogenic survival of the human skin fibroblasts was increased approximately 40% as compared to the untreated cells. The addition of peptide P1 had just as pronounced an effect as the addition of complete BBI, and the addition of peptides P2 and P3 yielded an even more pronounced effect, a further 20% greater than that of complete BBI.

Fragment P4, which differs from peptide P3 by having the serine base replaced with valine, exhibited less of an effect than complete BBI on clonogenic survival of the fibroblasts. Compared to the control (0), however, even the addition of P4 significantly increased the clonogenic survival of the skin fibroblasts.

The experiments shown in FIGS. 5 and 6 prove that the peptides according to the present invention exert a radioprotective effect, both with respect to ionizing radiation and with respect to UV radiation, that is comparable to and in some cases even better than that of complete BBI.

The peptides according to the present invention are thus ideal for use as radioprotective agents.

EXAMPLE 4

Protease-inhibiting Activity of the Peptides According to the Present Invention

Figure 7:
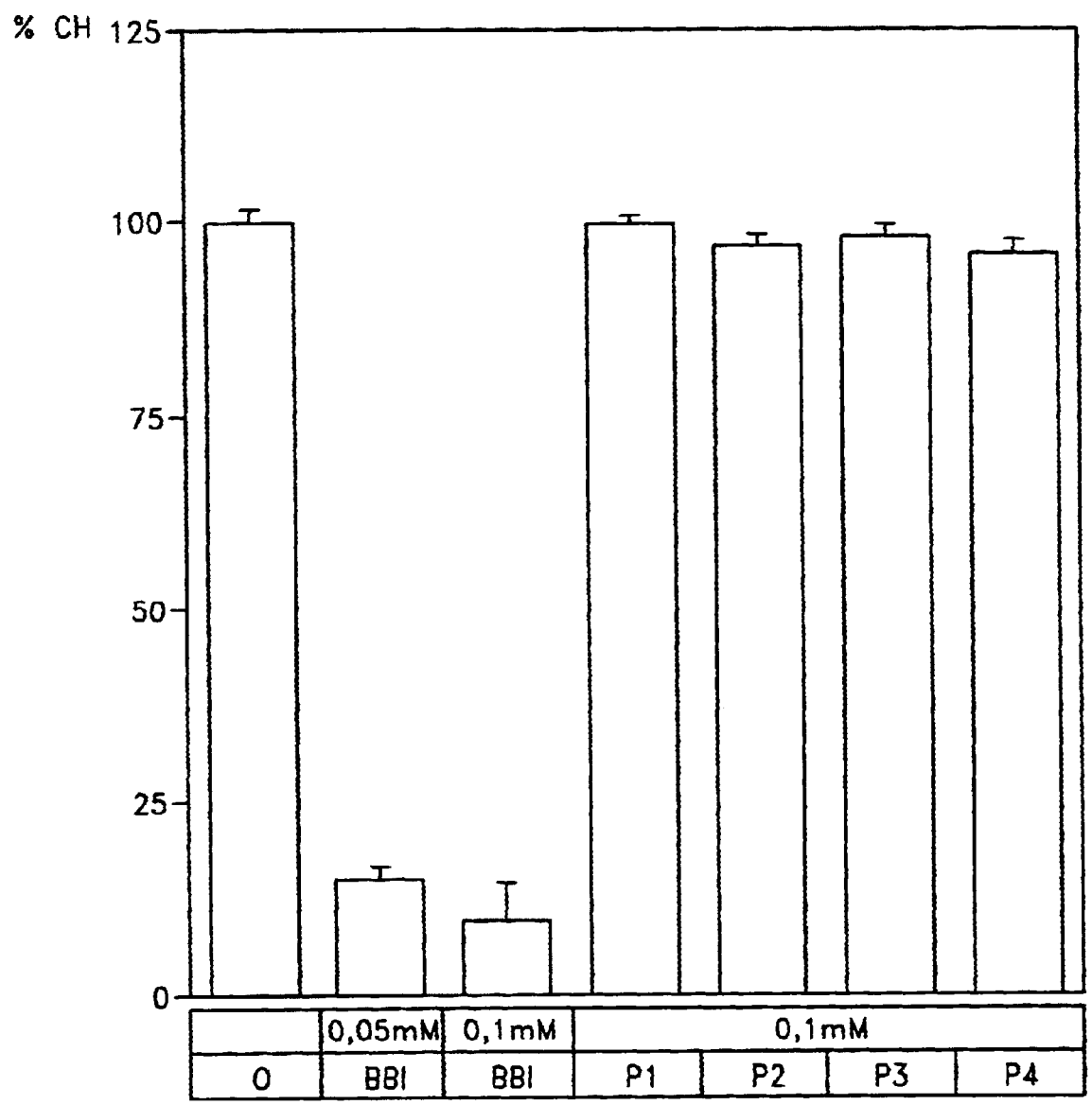
FIG. 7 shows, as a bar chart, the chymotrypsin-inhibiting activity of BBI and of four peptides according to the present invention.
Figure 8:
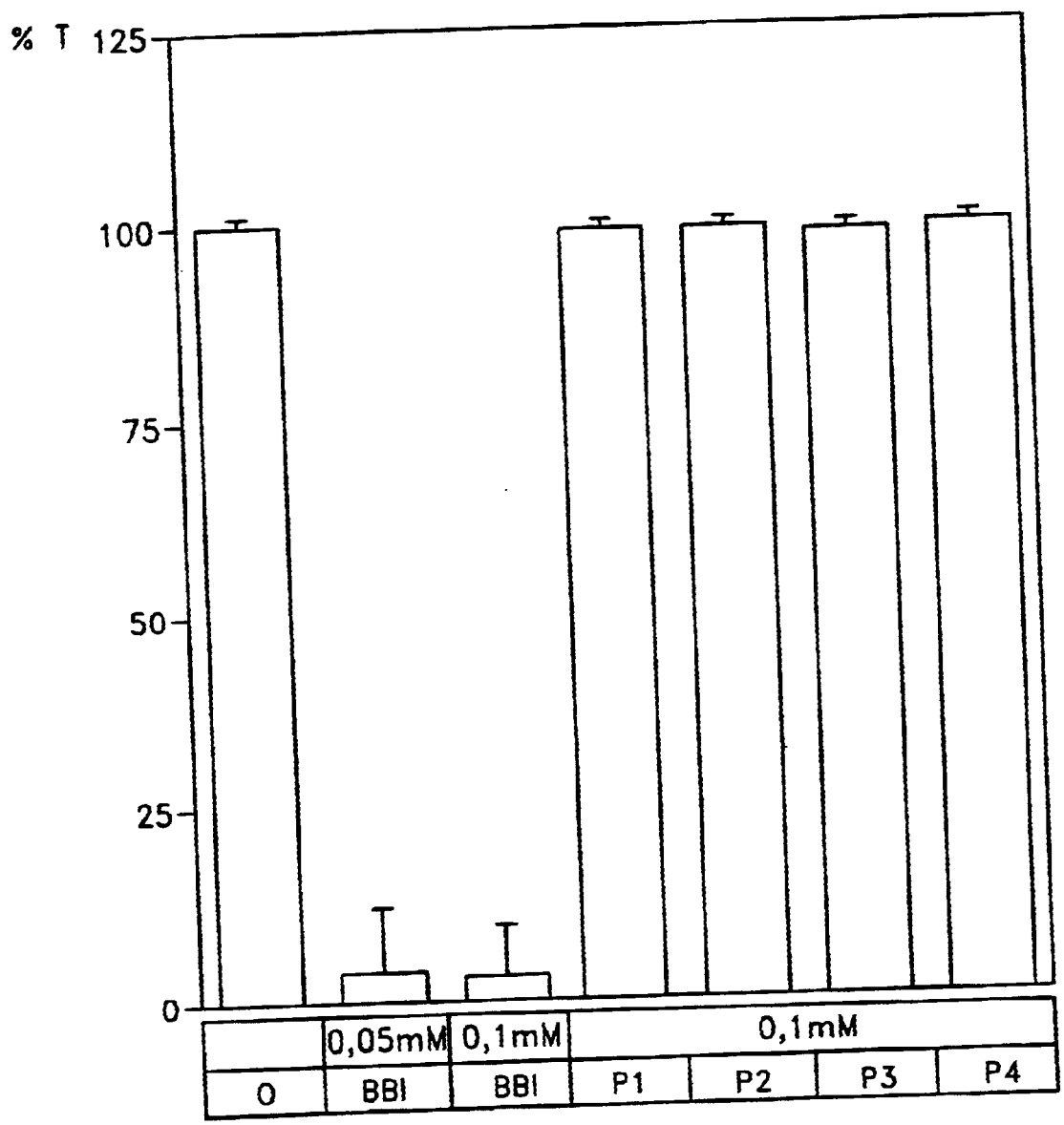
FIG. 8 shows, as a bar chart, the trypsin-inhibiting activity of BBI and of four peptides according to the present invention.

In the experiments whose results are shown in FIGS. 7 and 8, the protease-inhibiting activity of BBI was compared with that of the peptide fragments P1 through P4 that have already been discussed in Example 3.

The protease inhibition test was performed as described in section 1.3; FIG. 7 shows the inhibition of chymotrypsin, and FIG. 8 the inhibition of trypsin.

The control designated 0 indicates chymotrypsin and trypsin activity in the absence of both BBI and a peptide according to the present invention.

As is evident from FIG. 7, adding 0.05 mM and 0.1 mM of complete BBI (BBI) inhibits chymotrypsin activity by 80 and 90%, respectively. Compared to this, the addition of 0.1 mM of peptide P1, P2, P3, or P4 inhibits chymotrypsin activity by only a few percent or not at all.

As is apparent from the results shown in FIG. 8, the same applies to trypsin-inhibiting activity. Whereas complete BBI at a concentration of 0.05 mM or 0.1 mM inhibits the activity of trypsin by more than 90%, the addition of 0.1 mM of each of the peptides P1, P2, P3, or P4 has no effect on the activity of trypsin.

This Example shows that none of the peptides according to the present invention has an inhibiting effect on the proteases chymotrypsin or pepsin.

The peptides according to the present invention having a radioprotective effect therefore do not exhibit the undesirable side effect of also simultaneously blocking the digestive enzymes chymotrypsin and trypsin. As demonstrated in experiments with rats, blockage of these proteases, produced in the pancreas, by protease inhibitors results in severe damage to the pancreas.

The peptides according to the present invention are therefore suitable for use for radiation protection in humans, especially since the peptides P1 through P4, because of their small size, diffuse quickly and can therefore be easily distributed. Because of the small size of the peptides, immunological reactions are therefore also unlikely.

A particularly good effect is obtained with peptides P1 through P4 for protection against UV radiation, as shown in Example 3 in conjunction with FIG. 6. Since the peptides, comprising only nine or seven peptides, can in fact penetrate into the skin, they are particularly well suited for protecting human skin against elevated solar radiation.

What is claimed is:

1. An isolated or purified peptide having a radioprotective effect and having the amino acid sequence SEQ ID NO:2.

2. An isolated or purified peptide having a radioprotective effect and consisting of the amino acid sequence SEQ ID NO:3.

* * * * *